(12) United States Patent
Hansen (10) Patent No.: US 8,153,174 B2
(45) Date of Patent: Apr. 10, 2012

(54) FERMENTED PROTEIN PRODUCT

(75) Inventor: Ole Kaae Hansen, Ega (DK)

(73) Assignee: Hamlet Protein A/S, Horsens (DK)

( * ) Notice: Subject to any disclaimer, the term of this patent is extended or adjusted under 35 U.S.C. 154(b) by 729 days.

(21) Appl. No.: 11/392,925

(22) Filed: Mar. 30, 2006

(65) Prior Publication Data

US 2006/0233913 A1 Oct. 19, 2006

Related U.S. Application Data

(60) Provisional application No. 60/667,046, filed on Apr. 1, 2005.

(30) Foreign Application Priority Data

Apr. 1, 2005 (DK) .................................. 2005 00454

(51) Int. Cl.
*A23L 1/20* (2006.01)
(52) U.S. Cl. ........................................................ 426/46
(58) Field of Classification Search .................... 426/46
See application file for complete search history.

(56) References Cited

U.S. PATENT DOCUMENTS

| | | | |
|---|---|---|---|
| 2,190,644 A | 6/1937 | Rawling | |
| 3,632,346 A | 1/1972 | Sherba | |
| 3,803,329 A | 4/1974 | Valentas et al. | |
| 3,810,997 A * | 5/1974 | Chien | 426/46 |
| 4,008,334 A * | 2/1977 | Hansen | 426/46 |
| 4,085,229 A * | 4/1978 | Staron | 426/46 |
| 4,216,235 A * | 8/1980 | Dasek et al. | 426/46 |
| 4,409,256 A * | 10/1983 | Johnson et al. | 426/598 |
| 4,711,786 A | 12/1987 | Schmidt et al. | |
| 5,922,373 A | 7/1999 | Johnston et al. | |

FOREIGN PATENT DOCUMENTS

| | | |
|---|---|---|
| DE | 278 058 A1 | 4/1990 |
| EP | 0 486 738 A1 | 5/1992 |
| GB | 1 455 933 | 11/1976 |
| GB | 1 550 703 | 8/1979 |
| JP | 54 154552 A | 12/1979 |
| JP | 56 039744 A | 4/1981 |
| JP | 57 202256 A | 12/1982 |
| RO | 116 202 B | 11/2000 |
| SU | 1 214 053 A | 2/1986 |
| SU | 1 297 789 A | 3/1987 |

OTHER PUBLICATIONS

Hashimoto et al. JP 61 104759—The English abstract is at the lat two pages.*
Boisen and Moughan; "Different Expressions of Dietary Protein and Amino Acid Digestibility in Pig Feeds and Their Application in Protein Evaluation; a Theoretical Approach"; Acta Agriculture Scandinavica Sect. A Animal Science 1996; 46, 165-172.
Sigurd Boisen; "A New Protein Evaluation System for Pig Feeds and Its Practical Application"; Acta Agriculture Scandinavica Sect. A Animal Science 1998; 48, 1-11.
Hans Christian Elbek Pedersen; "Studies of Soyabean Protein Intolerance in the Preruminant Calf"; Thesis submitted to the University of Reading, Sep. 1986.

* cited by examiner

*Primary Examiner* — D. Lawrence Tarazano
*Assistant Examiner* — Hamid R Badr
(74) *Attorney, Agent, or Firm* — Foley & Lardner LLP (57) ABSTRACT

The present invention relates to protein products with improved nutritional value, and enhanced organoleptic properties, and uses thereof. In particular, the present invention provides fermented protein rich products on basis of fermented pulses and yeast, wherein the fermentation is followed by a heating step.

74 Claims, 1 Drawing Sheet

FERMENTED PROTEIN PRODUCT

This is a complete application claiming the priority of U.S. Provisional Application 60/667,046 filed 1 Apr. 2005 and Danish Application PA 2005 00454 filed 1 Apr. 2005.

FIELD OF THE INVENTION

The present invention relates to a fermented protein product derived from yeast and proteinaceous pulse parts, having the advantage of possessing good nutritional properties and at the same time enhanced organoleptic properties.

BACKGROUND OF THE INVENTION

The continued increase in world population has accentuated the demand for proteins suitable for human food and animal feed. At the same time, use of traditional sources such as fish or livestock is being restricted due to health concern and/or limited supply.

It is well known that certain vegetable crops can provide proteins of high quality. Unfortunately, however, such crops frequently contain harmful and/or bad tasting components that make them unsuitable for food and feed purposes without further treatment. This is especially the case for pulses and in the following soya beans will be used as an example.

Raw soya beans have a content of biologically active proteins known as trypsin inhibitors. They reduce the activity of trypsin which is an enzyme needed in the digestive process. The result is a reduction in nutritional value of the soya-based product. The content of the trypsin inhibitors can be reduced by a heating process, which on the other hand might lead to a reduced value of the soya protein.

Another group of biologically active proteins are the antigens of which the most important are identified as being glycinin and β-conglycinin. They are known to induce serious allergic reactions, especially in young mammals where the digestive tract is not yet fully developed. The known methods to inactivate these proteins are by treating with water-alcohol mixtures and/or by a heating process. The denaturation of the proteins caused by these treatments will result in products with a reduced ability to bind water and fat, as well as overheating may impair the nutritional quality.

The amount and nature of carbohydrates is another group of constituents of concern. Especially the α-1,6-galactosides are of concern as they provoke flatulence and diarrhoea. Means to reduce or eliminate the content of α-1,6-galactosides are extraction with water, degradation by the action of specific enzymes or fermentation. All in all, this is associated with an unfavourable cost benefit ratio.

Furthermore, the palatability of the product is essential for the application of such a product in food and feed. Thus, crude protein products based on pulses are associated with an unpleasant "beany" taste. Processing such as heat treatment add/or extraction with water-alcohol mixtures can reduce this. Commercially available product categories with improved flavour are protein concentrates and isolates.

The main drawbacks of these products are that they are expensive to manufacture and—although they may have a bland taste—they do not possess an attractive flavour on their own that stimulates the appetite. This demonstrates the need for a new type of product, which at the same time is nutritionally optimised and has good functional properties and an attractive flavour.

DESCRIPTION OF PRIOR ART

U.S. Pat. No. 2,190,644 discloses a method for separation of carbohydrates from the proteins of a substantially oil-free soya bean meal. The method comprises the steps of subjecting the soya bean meal to the action of yeast to convert the carbohydrates into alcohol and carbon dioxide, removing the alcohol by steaming under vacuum to prevent the temperature from exceeding 85° C.

U.S. Pat. No. 3,632,346 discloses a method for the elimination of flatulence-producing saccharides in foodstuffs by contacting them with an enzyme preparation capable of hydrolysing the α-1,6-linkages of stachyose. The process is further directed towards foodstuffs made on the basis of soya bean e.g. soya milk.

U.S. Pat. No. 3,803,329 discloses a method for the production of a bland, textured soya protein product. The vegetable protein raw material is moistened to a water content of 20-35% by weight and fermented to break down carbohydrates and to modify the flavour and improve blandness. The fermentation step is performed in the presence of 0.5-2.5% added yeast and optionally an enzyme. Feeding it to a processing zone with a pressurised gaseous processing fluid textures the fermented protein material. After the fermentation the total sugar level is reduced by about 50%. The reduction in "beany" taste is probably due to the water vapour distillation in the texturising step in the process. Nothing is mentioned about an improved flavour.

GB 1 455 933 discloses a method for producing textured protein, which comprises fermenting a vegetable protein material being in a granular or particulate form and having a moisture content of 20% to 35% by weight, and then texturizing the fermented material by treatment with hot pressurized steam. Soy material or other vegetable protein material having a moisture content of from 20 to 35% by weight is fermented in the presence of yeast or other fermentation microorganism and optionally in the presence of an enzyme.

In the description of GB 1 455 933 it is explained that the incubation must be at a temperature of at least 40° F. (4.4° C.), preferably 75 to 125° F. (24 to 52° C.), generally about 100° F. (38° C.), and typically the incubation period will be about 24 to 43 hours or longer. The maximum pressure used in the steam treatment may be as high as 140 p.s.i.g. (1 MPa gauge) and as low as 15 p.s.i.g. (103 kPa gauge), and thus the temperature during steam treatment will generally be at least 250° F. (121° C.) and may be as high as 500° F. (260° C.). In the description it is specified that the soya material or other vegetable protein material is treated to reduce the soya flavor and that also the level of stachyose and raffinose (recognized for producing flatulence) is substantially reduced.

GB 1 550 703 discloses a method for the production of a deflatulated soya product, which comprises fermenting defatted soya meal in an aqueous mash containing 25-60% water by weight with non-dried live brewer's bottom yeast for a time of 100-300 minutes at 40-65° C. Fermentation is followed by a brief sterilization step.

U.S. Pat. No. 4,216,235 discloses a process for eliminating flatulent carbohydrates in an aqueous soya suspension containing from 5-45% by weight of dry matter, inoculating the suspension with at least one strain of Saccharomyces uvarum which has reached the state of growth on a medium containing at least one sugar having at least one α-D-galactopyranosyl bond and fermenting the suspension under anaerobic conditions for at least 8 hours at a temperature of 15-50° C. Only a modest quantity of yeast is produced in the suspension. Fermentation is followed by pasteurization or by drying.

U.S. Pat. No. 5,922,373 discloses a process for preparing a soya protein feed with enhanced nutritional value. The method comprises: Combining soya flour, sugar and water; gelatinising the carbohydrate in the soya flour of the mixture; reacting the gelatinised mixture with yeast to reduce the allergic properties of the soya flour, and terminating the reaction to provide a modified soya flour feed. The yeast is added to the gelatinised mixture at a weight of 0.25-15%.

U.S. Pat. No. 4,008,334 discloses a method for removal of substantially all of the water-soluble carbohydrates in the production of plant protein products. An aqueous solution or dispersion of the plant material containing 1-60% of dry matter is fermented with particular strains of *Saccharomyces* at a temperature of 20-40° C. and at a pH of 4-7 for 12-48 hours. Drying of the product may follow fermentation.

DD 278 058 A1 discloses a method for microbial treatment of oilseeds and legumes in which fat-containing or defatted raw materials, preferably soya beans and broad beans, under specific buffer conditions are subjected to a 6 to 24 hours action of mixed cultures of *Lactobacillus plantarum* and *Lactobacillus coryniformis* as well as *Saccharomyces cerevisiae* and *Oospora lactis*, preferably in the form of dried sourdough or leavened dough, in amounts of 1.0 to 16.0% (weight/volume) based on the dry matter of the raw materials, and as growth-stimulators either carbohydrate digesting enzyme complexes or, alternatively, exogenous carbon- and nitrogen-sources and, optionally, polyanionic compounds destined to form insoluble protein complexes are added, and thereafter a pasteurisation, concentration and/or drying is performed.

In the description of DD 278 058 A1 it is explained that the treatment with lactic acid bacteria and yeast results in a decomposition of substances causing flatulence and off-flavour in particular in soya as well as glucosinolates and phenolic acid from oilseeds such as rapeseed and sunflower. As to soya the treatment leads to an improvement of flavour and consistency characteristics in a range of products. From the text it appears that a necessary prerequisite for obtaining such improved characteristics is that a pH which is above the isoelectric point (preferably between 5.0 and 6.0) is maintained in the first phase of fermentation, and a pH which is below the isoelectric point (preferably between 3.0 and 4.0) is maintained in the second phase of fermentation. Another necessary prerequisite is that enzymes in the form of cellulases and/or amylases or, alternatively, extraneous carbon- and nitrogen-sources from vegetable or animal waste materials such as potato fruit water, molasses and whey, are added in amounts of 2-20% based on the dry matter of the raw materials. From the three Examples, showing defatted soya meal, horse beans and lupine, respectively, it appears that the dry matter content of the starting material is in the range of 11-17%.

None of the documents mentioned above provide fermented protein products having the following features:
- An attractive flavour stimulating the appetite, high digestibility, and excellent functional properties such as e.g. water and lipid binding capacity.
- Significantly reduced level of relevant anti-nutritional factors.
- Providing cost efficient methods of obtaining products having the above mentioned desired properties.

OBJECTS OF THE INVENTION

One object of the invention is to provide a fermented protein product where one or more types of yeast and one or more proteinaceous pulse sources constitute the protein part of the product.

Another object is that the fermented protein product may further comprise varying amounts of lipids e.g. glycerides, lecithin, etc., associated with or added to the proteinaceous pulse sources.

Yet a further object is that the product at the same time has an attractive flavour, high digestibility and excellent functional properties e.g. water binding capacity.

SUMMARY OF THE INVENTION

These objects are surprisingly fulfilled by the methods and the products of the present invention.

The present invention thus relates to a fermented protein product derived from yeast and proteinaceous pulse parts, wherein the protein content of said product is about 25-80% by weight on dry matter basis, and about 1-35% of the protein content is derived from yeast and about 65-99% of the protein content is derived from proteinaceous pulse parts, and wherein the glyceride content is max. 30% by weight, preferably 0.5-23% by weight on dry matter basis, said product comprising the following features:
- the content of at least one anti-nutritional factor selected from the group consisting of trypsin inhibitors, antigens, flatulence-producing oligosaccharides such as $\alpha$-1,6-galactosides, phytic acid, and lectins is reduced by 50% or more, preferably by 75% or more, more preferably by 90% or more, even more preferably by 95% or more, and most preferably by 99% or more as compared to the unprocessed pulse parts;
- at least one compound selected from the group consisting of 1-pentanol, 1-hexanol, and 1-octen-3-ol is reduced by 50% or more, preferably by 75% or more, more preferably by 90% or more, even more preferably by 95% or more, and most preferably by 99% or more as compared to the unprocessed pulse parts;
- at least one compound selected from the group consisting of 3-hydroxy-2-butanone, 3-methyl-1-butanol, ethyl octanoate, and ethyl decanoate is formed or is increased by 10% or more, preferably 20% or more, more preferably 30% or more, even more preferably 40% or more, and most preferably 50% or more as compared to the unprocessed pulse parts.

In another aspect the invention relates to a fermented protein product derived from yeast and proteinaceous pulse parts, wherein the protein content of said product is about 25-80% by weight on dry matter basis, and about 1-35% of the protein content is derived from yeast and about 65-99% of the protein content is derived from proteinaceous pulse parts, and wherein the glyceride content is max. 30% by weight, preferably 0.5-23% by weight on dry matter basis, said product comprising the following features:
- the content of anti-nutritional factors selected from the group consisting of trypsin inhibitors, antigens, flatulence-producing oligosaccharides such as $\alpha$-1,6-galactosides, phytic acid, and lectins is reduced by 50% or more, preferably by 75% or more, more preferably by 90% or more, even more preferably by 95% or more, and most preferably by 99% or more as compared to the unprocessed pulse parts;
- the content of beany flavour components selected from the group consisting of 1-pentanol, 1-hexanol, and 1-octen-3-ol is max. 10% rpa, preferably not more than 5% rpa, more preferably not more than 3% rpa, and most preferably not more than 1.5% rpa, where rpa is the relative peak area measured by headspace chromatography of the total compounds volatile at 70° C.;
- the content of attractive flavour components selected from the group consisting of 3-hydroxy-2-butanone, 3-methyl-1-butanol, ethyl octanoate, and ethyl decanoate is min. 5% rpa, preferably at least 8% rpa, more preferably at least 10% rpa, even more preferably at least 15% rpa, and most preferably at least 20% rpa, where rpa is the relative peak area measured by headspace chromatography of the total compounds volatile at 70° C.

Preferably, the yeast portion of the fermented protein product according to the invention is of the *Saccharomyces cerevisiae* type, and most preferably brewer's yeast; and the pulse parts portion preferably originates from soya, pea, lupine, a mixture of soya and pea, a mixture of soya and lupine, a mixture of pea and lupine, or a mixture of soya, pea and lupine.

Preferably, the product according to the invention has been subjected to full or partial drying, preferably to a water content of not more than 10% by weight and a water binding capacity of at least 4 parts per part of the product by weight. It has a standard ileal digestibility measured in pigs of at least 90%, and it may further comprise one or more edible ingredients.

In a further aspect, the present invention relates to a method of preparing a fermented protein product as described above comprising the following steps:
(i) mixing live yeast with proteinaceous pulse parts in a dry matter ratio of from about 1:2 to 1:100;
(ii) fermenting the yeast/pulse mixture resulting from step (i) under conditions where the water content does not exceed 80%, for 1-12 hours at a temperature of about 25-60° C., preferably of about 25-45° C., under anaerobic conditions; and
(iii) incubating the fermented mixture resulting from step (ii) for 0.5-240 minutes at a temperature of about 70-150° C. in a closed system.

In a still further aspect the present invention relates to a method of preparing a fermented protein product as described above comprising the following steps:
(i) mixing live yeast with proteinaceous pulse parts in a dry matter ratio of from about 1:2 to 1:100;
(ii) fermenting the yeast/pulse mixture resulting from step (i) under conditions where the water content does not exceed 80%, for 1-12 hours at a temperature of about 25-60° C., preferably about 25-45° C., under anaerobic conditions;
(iii) fermenting the yeast/pulse mixture resulting from step (ii) under conditions where the water content does not exceed 80%, for 1-12 hours at a temperature of about 25-60° C., preferably about 30-60° C., under aerobic conditions; and
(iv) incubating the fermented mixture resulting from step (iii) for 0.5-240 minutes at a temperature of about 70-150° C. in a closed system.

In connection with any of the steps in the above methods may be added one or more enzymes selected from the group consisting of proteases, peptidases, galactosidases, amylases, pectinases, hemicellulases, phytases, lipases, and phospholipases.

The mixture obtained in the last step of either of the above methods may be subjected to drying and milling under such conditions that the particle temperature does not exceed 100° C., preferably 85° C., more preferably 80° C., and most preferably 70° C., preferably to obtain a product having a water content of not more than 10% by weight and a water binding capacity of at least 4 parts per part of the product by weight.

The present invention furthermore relates to various uses of a fermented protein product according to the invention.

BRIEF DESCRIPTION OF THE DRAWINGS

The identification of the flavour components is listed in the following table.

| Component | Retention time in minutes |
| --- | --- |
| 1-pentanol | 18.19 |
| 1-hexanol | 20.75 |
| 1-octen-3-ol | 23.34 |
| 3-hydroxy-2-butanone | 16.74 |
| 3-methyl-1-butanol | 17.40 |
| Ethyl octanoate | 27.48 |
| Ethyl decanoate | 30.80 |

Figure 1:
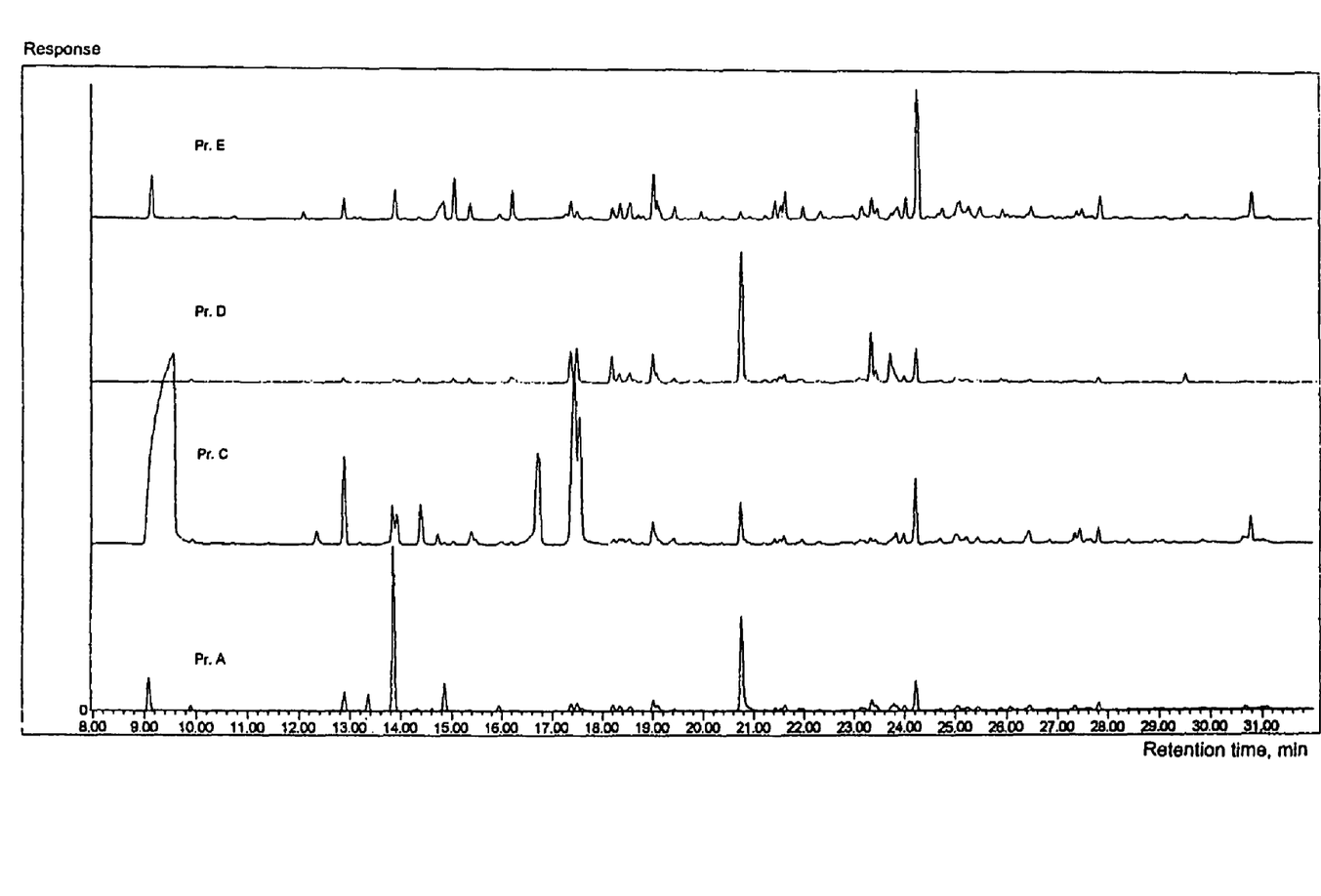
FIG. 1: Illustrates the flavour characteristics of fermented protein products according to the invention in comparison with the unfermented vegetable protein source. Product A is defatted, toasted soya beans. Product C is a product based on aforementioned A according to the invention. Product D is whole, toasted soya beans. Product E is a product based on the aforementioned D according to the invention. Flavour changes are illustrated in a comparative headspace chromatogram made according to the specifications given in Example 7. The peaks were identified by mass spectroscopy.

As can be seen in FIG. 1 the "beany" flavouring components 1-pentanol, 1-hexanol and 1-octen-3-ol are reduced, and the favourable flavouring components 3-hydroxy-2-butanone, 3-methyl-1-butanol, ethyl octanoate and ethyl decanoate are formed and/or increased.

Definitions

Improved functional properties: Food or feed products according to the invention, made partly on basis of pulses, having improved functional properties is herein understood as products with very low or no tendency of causing diarrhoea, flatulence, and allergy achieved by a reduced content of anti-nutritional factors. The product furthermore has a reduced beany flavour and an increased attractive flavour and excellent water and lipid binding properties. Food products according to the invention with improved functional properties are thus well suited for food or feed for any human or animal, such as milk replacers, and are particularly well suited for feeding to individuals at risk of or having allergy and/or individuals with immature and/or sensitive digestive tracts.

Processed food products: Comprise dairy products, processed meat products, sweets, desserts, ice cream desserts, canned products, freeze dried meals, dressings, soups, convenience food, bread, cakes, etc.

Processed feed products: Comprise ready-to-use feed for animals such as piglets, calves, poultry, furred animals, sheep, cats, dogs, fish and crustaceans etc.

Pharmaceutical products: Comprise products, typically in the form of a tablet or in granulated form, containing one or more biologically active ingredients intended for curing and/or alleviating the symptoms of a disease or a condition. Pharmaceutical products furthermore comprise pharmaceutically acceptable excipients and/or carriers. The protein products herein disclosed are very well suited for use as a pharmaceutically acceptable ingredient in a tablet or granulate.

Cosmetic products: Comprise products intended for personal hygiene as well as improved appearance such as conditioners and bath preparations.

DETAILED DESCRIPTION OF THE INVENTION

In a first aspect, the present invention thus relates to a fermented protein product derived from yeast and proteinaceous pulse parts, wherein the protein content of said product is about 25-80% by weight on dry matter basis, and about 1-35% of the protein content is derived from yeast and about 65-99% of the protein content is derived from proteinaceous pulse parts, and wherein the glyceride content is max. 30% by weight, preferably 0.5-23% by weight on dry matter basis, said product comprising the following features:

the content of at least one anti-nutritional factor selected from the group consisting of trypsin inhibitors, antigens, flatulence-producing oligosaccharides such as α-1,6-galactosides, phytic acid, and lectins is reduced by 50% or more, preferably by 75% or more, more preferably by 90% or more, even more preferably by 95% or more, and most preferably by 99% or more as compared to the unprocessed pulse parts;

at least one compound selected from the group consisting of 1-pentanol, 1-hexanol, and 1-octen-3-ol is reduced by 50% or more, preferably by 75% or more, more preferably by 90% or more, even more preferably by 95% or more, and most preferably by 99% or more as compared to the unprocessed pulse parts;

at least one compound selected from the group consisting of 3-hydroxy-2-butanone, 3-methyl-1-butanol, ethyl octanoate, and ethyl decanoate is formed or is increased by 10% or more, preferably 20% or more, more preferably 30% or more, even more preferably 40% or more, and most preferably 50% or more as compared to the unprocessed pulse parts.

In a second aspect, the present invention relates to a fermented protein product derived from yeast and proteinaceous pulse parts, wherein the protein content of said product is about 25-80% by weight on dry matter basis, and about 1-35% of the protein content is derived from yeast and about 65-99% of the protein content is derived from proteinaceous pulse parts, and wherein the glyceride content is max. 30% by weight, preferably 0.5-23% by weight on dry matter basis, said product comprising the following features:

the content of anti-nutritional factors selected from the group consisting of trypsin inhibitors, antigens, flatulence-producing oligosaccharides such as α-1,6-galactosides, phytic acid, and lectins is reduced by 50% or more, preferably by 75% or more, more preferably by 90% or more, even more preferably by 0.95% or more, and most preferably by 99% or more as compared to the unprocessed pulse parts;

the content of beany flavour components selected from the group consisting of 1-pentanol, 1-hexanol, and 1-octen-3-ol is max. 10% rpa, preferably not more than 5% rpa, more preferably not more than 3% rpa, and most preferably not more than 1.5% rpa, where rpa is the relative peak area measured by headspace chromatography of the total compounds volatile at 70° C.;

the content of attractive flavour components selected from the group consisting of 3-hydroxy-2-butanone, 3-methyl-1-butanol, ethyl octanoate, and ethyl decanoate is min. 5% rpa, preferably at least 8% rpa, more preferably at least 10% rpa, even more preferably at least 15% rpa, and most preferably at least 20% rpa, where rpa is the relative peak area measured by headspace chromatography of the total compounds volatile at 70° C.

In a preferred embodiment of the present invention, the yeast is preferably of the *Saccharomyces cerevisiae* type, and most preferably brewer's yeast. The proteinaceous pulse parts preferably originate from soya and/or pea and/or lupine.

Also, in a preferred embodiment of the present invention, the fermented protein product has a standard ileal digestibility measured in pigs of at least 90%.

In a third aspect, the present invention relates to a method of preparing a fermented protein product derived from yeast and proteinaceous pulse parts as described above comprising the following steps:
(i) mixing live yeast with proteinaceous pulse parts in a dry matter ratio of from about 1:2 to 1:100;
(ii) fermenting the yeast/pulse mixture resulting from step (i) under conditions where the water content does not exceed 80%, for 1-12 hours at a temperature of about 25-60° C., more preferably of about 25-45° C., under anaerobic conditions; and
(iii) incubating the fermented mixture resulting from step (ii) for 0.5-240 minutes at a temperature of about 70-150° C. in a closed system.

In a fourth aspect, the present invention relates to a method of preparing a fermented protein product derived from yeast and proteinaceous pulse parts as described above comprising the following steps:
(i) mixing live yeast with proteinaceous pulse parts in a dry matter ratio of from about 1:2 to 1:100;
(ii) fermenting the yeast/pulse mixture resulting from step (i) under conditions where the water content does not exceed 80%, for 1-12 hours at a temperature of about 25-60° C., more preferably of about 25-45° C., under anaerobic conditions;
(iii) fermenting the yeast/pulse mixture resulting from step (ii) under conditions where the water content does not exceed 80%, for 1-12 hours at a temperature of about 25-60° C., more preferably of about 30-60° C., under aerobic conditions; and
(iv) incubating the fermented mixture resulting from step (iii) for 0.5-240 minutes at a temperature of about 70-150° C. in a closed system.

In a preferred embodiment of the methods of the invention, one or more enzymes selected from the group consisting of proteases, peptidases, galactosidases, amylases, pectinases, hemicellulases, phytases, lipases, and phospholipases are added in connection with any of the steps in the above methods. The fermented protein product obtained in the last step may furthermore be subjected to drying and milling under such conditions that the particle temperature does not exceed 100° C., preferably 85° C., more preferably 80° C., and most preferably 70° C.

In another preferred embodiment of the methods of the invention, the fermented protein product is subjected to full or partial drying, preferably to obtain a product having a water content of not more than 10% by weight and a water binding capacity of at least 4 parts per part of the product by weight. The fermented protein product furthermore preferably comprises a protein content of 25-80% by weight on dry matter basis and a glyceride content of 0-30% by weight, more preferably 0.5-23% by weight, on dry matter basis. Preferably, about 1-35% of the protein content is derived from yeast protein and about 65-99% is derived from pulse proteins.

In a specific embodiment of the methods of the invention, the content of at least one anti-nutritional factor selected from the group consisting of trypsin inhibitors, antigens, flatulence-producing oligosaccharides such as α-1,6-galactosides, phytic acid, and lectins is reduced by 50% or more, preferably by 75% or more, more preferably by 90% or more, even more preferably by 95% or more, and most preferably by 99% or more as compared to the unprocessed proteinaceous pulse parts. Also, at least one constituent selected from the group consisting of 1-pentanol, 1-hexanol, and 1-octen-3-ol is reduced by 50% or more, preferably by 75% or more, more preferably by 90% or more, even more preferably by 95% or more, and most preferably by 99% or more as compared to the unprocessed proteinaceous pulse parts. Further, at least one constituent selected from the group consisting of 3-hydroxy-2-butanone, 3-methyl-1-butanol, ethyl octanoate, and ethyl decanoate is formed or is increased by 10% or more, preferably by 20% or more, more preferably by 30% or more, even more preferably by 40% or more, and most preferably by 50% or more as compared to the unprocessed pulses.

In another specific embodiment of the methods of the invention, the content of anti-nutritional factors selected from the group consisting of trypsin inhibitors, antigens, flatulence-producing oligosaccharides such as α-1,6-galactosides, phytic acid, and lectins is reduced by 50% or more, preferably by 75% or more, more preferably by 90% or more, even more preferably by 95% or more, and most preferably by 99% or more as compared to the unprocessed proteinaceous pulse parts. Also, the content of beany flavour components selected from the group consisting of 1-pentanol, 1-hexanol, and 1-octen-3-ol is reduced to max. 10% rpa, preferably not more than 5% rpa, more preferably not more than 3% rpa, and most preferably not more than 1.5% rpa, where rpa is the relative peak area measured by headspace chromatography of the total compounds volatile at 70° C. Further, attractive flavour components selected from the group consisting of 3-hydroxy-2-butanone, 3-methyl-1-butanol, ethyl octanoate, and ethyl decanoate are newly formed or increased to a content of min. 5% rpa, preferably at least 8% rpa, more preferably at least 10% rpa, even more preferably at least 15% rpa, and most preferably at least 20% rpa, where rpa is the relative peak area measured by headspace chromatography of the total compounds volatile at 70° C.

In another embodiment according to the present invention, one or more edible ingredients are added to the product.

In a further aspect, the present invention relates to the use of a fermented protein product as described above for the manufacture of a processed food product for human and/or animal consumption. The invention also relates to the use of such product for the manufacture of a processed food or feed product with improved functional properties. Specifically, the invention relates to the use of such product for the manufacture of a food or feed product for individuals with a sensitive digestive tract and/or individuals having or being at risk of developing allergy. Further, the invention relates to the use of such product for the manufacture of a cosmetic or a pharmaceutical product.

A number of steps must be performed in connection with the methods of the present invention:
  Mixing live yeast with proteinaceous pulse parts;
  Fermenting the yeast/pulse mixture;
  Heat-treating the fermented mixture.

Fermenting with live yeast: Fermentation is carried out with yeast cells of the *Pichia* type (e.g. *Pichia pastoris*), the fission type (*Schizosaccharomyces*) or the budding type (*Saccharomyces*). *Saccharomyces cerevisae* is the most preferred yeast type. "Baker's yeast" or "brewer's yeast" as used herein refer to a large number of *Saccharomyces* types, such as e.g. *Saccharomyces cerevisiae* or *Saccharomyces carlsbergensis*. Spent brewer's or baker's yeast refers to waste products from industrial productions. The skilled person knows that a wide variety of yeast strains are available, including strains that have e.g. thermophilic features, etc. One or more enzymes can be added, such as proteases, peptidases, galactosidases, amylases, pectinases, hemicellulases, phytases, phospholipases, and lipases. Yeast may be added in a yeast/pulse dry matter ratio of from about 1:100 to about 1:2. Ratios such as: 1:2; 1:3; 1:4; 1:5; 1:6; 1:7; 1:8; 1:9; 1:10; 1:20; 1:30; 1:40; 1:50; 1:60; 1:70; 1:80; 1:90; and 1:100 are thus included. The advantage of using high yeast ratios is that the final product becomes enriched with proteins with a complementary amino acid profile, and that a relatively short fermentation time and a relatively low fermentation temperature is required. Furthermore, yeast provides valuable trace components e.g. vitamins, nucleotides, mannans and glucans, etc.

Fermentation may optionally be carried out in a two-step process. The first step comprises fermentation under anaerobic conditions. This will ensure enzymatic degradation of anti-nutritional factors such as oligosaccharides and conversion of offensive flavour notes. The second step is preferably carried out aerobically, ensuring yeast proliferation and complete decomposition of the partially degraded carbohydrates. Furthermore, a partial drying of the resulting product may thus be obtained.

Pulses: The plant material used as a starting material is in the form of proteinaceous parts from pulses. The plant material may be milled, pulverised or otherwise divided into particles. Examples of pulses include: soya beans, peas, and lupines.

Mixing: Mixing yeasts, pulses, and water can in principle be performed by any manual or automatic means known to a person skilled in the art.

Water content: The water content during processing of the plant protein product is 80% or less, preferably 60% or less. After heat treatment, the water content may be reduced to about 10% by weight or less.

Fermentation temperature: The temperature during the fermentation step is from about 25 to about 60° C., thus including 25, 26, 27, 28, 29, 30, 31, 32, 33, 34, 35, 40, 45, 50, 55, and 60° C. In the case that two-step fermentation is carried out, the temperature in the first step is preferably in the range of 25-45° C., and in the second step it is preferably in the range of 30-60° C.

Duration of the fermentation step: The pulse/yeast mixture may be fermented for 1-12 hours, including 1, 2, 3, 4, 5, 6, 7, 8, 9, 10, 11, and 12 hours.

Heat treatment after fermentation: Heat treatment of the fermented product should be carried out in a closed system at about 70-150° C., preferably 85-150° C., including 70, 75, 80, 85, 86, 87, 88, 89, 90, 91, 92, 93, 94, 95, 96, 97, 98, 99, 100, 105, 110, 115, 120, 125, 130, 135, 140, 145, 150° C. for 0.5-240 minutes, preferably 6-240 minutes, including 0.5, 1, 2, 3, 4, 5, 6, 7, 8, 9, 10, 15, 20, 25, 30, 35, 40, 45, 50, 55, 60, 90, 120, 150, 180, 210, and 240 minutes. The purpose of the heat treatment is to kill all microorganisms and to inactivate remaining anti-nutritional factors, without impairing the quality of the protein part.

When choosing conditions for the heat treatment the skilled person knows that when using very high temperatures, relatively short incubation times are needed.

The inventor has found that by applying the processing steps as described, including the heat treatment at relatively high temperatures on the fermented proteinaceous pulse parts as well as proteins and other accompanying components from yeast, the resulting product possesses favourable organoleptic properties. This is very surprising and to give an explanation of the underlying mechanisms would be speculative at this stage.

After treatment: After the heat treatment the fermented protein product may be dried to a water content of 10% by weight or less, preferably 8% or less. The drying should be carried out under such conditions that the particle temperature does not exceed 100° C., preferably 85° C., more preferably 80° C., and most preferably 70° C. Drying increases shelf life and facilitates handling. The dried product may optionally be milled.

One or more edible ingredients may subsequently be added to the product, such as e.g. carbohydrates, proteins, acylglycerols, emulsifiers, mineral salts, vitamins, amino acids, pH buffering substances, colours, preservatives, and flavours.

The product: Products of the invention surprisingly turn out to have a very attractive flavour. It is demonstrated that the improved flavour is due to a significant reduction in the content of components causing unpleasant flavour, and/or the formation of and/or an increase in the content of components causing attractive flavour.

The resulting products furthermore have excellent nutritional properties. Thus, a standard ileal digestibility of min. 90%, preferably min. 92%, more preferably min. 94% is obtained (measured in pigs, according to the method described in Boisen, S., Acta. Agric. Scand., Sect. A, Animal Science 1998: 48, 1-11 and Boisen, S. & Maughan, P. J., Acta. Agric. Scand., Sect. A, Animal Science 1996: 46, 165-172). The improved digestibility correlates with a significant reduction of the content of anti-nutritional factors according to this invention.

Fermented protein products according to the present invention are useful as a food product for humans and animals but also in production of cosmetic and pharmaceutical products. Pharmaceutical and cosmetic products might contain between 1 and 99% of the protein product.

In food and feed the normal use concentrations are about 1-5% when used as a functional ingredient and about 5-99% when used as a nutritional ingredient.

Anti-nutritional factors: Comprise compounds such as trypsin inhibitors, antigens, flatulence-producing oligosaccharides, phytic acid and lectins (see for example H. C. Elbek Pedersen: "Studies of Soyabean Protein Intolerance in the Preruminant Calf, University of Reading September 1986, pp. 44 and 48-55). Anti-nutritional factors are reduced by at least 50%, preferably by at least 75%, more preferably by at least 90%, and most preferably by at least 95% as compared to the unprocessed pulse parts.

Beany flavour: In the literature (Goossens, Food Engineering October 1974, pp. 59-60) components such as 1-pentanol, 1-hexanol and 1-octen-3-ol are reported as major contributors to the beany flavour of pulses such as soya. This off-flavour is unwanted in a fermented protein product that is to be used as an ingredient in food, feed, cosmetic and pharmaceutical products. Beany flavour components are reduced by at least 50%, preferably by at least 75%, more preferably by at least 90%, and most preferably by at least 95% as compared to the unprocessed pulse parts. Based on FIG. 1, the content of beany flavour components in a product of the invention is max. 10% rpa, preferably not more than 5% rpa, more preferably not more than 3% rpa, and most preferably not more than 1.5% rpa, where rpa is the relative peak area measured by headspace chromatography of the total compounds volatile at 70° C.

Attractive flavour: Attractive flavour components are for example
- 3-hydroxy-2-butanone which has a fruity, mouldy, woody flavour,
- 3-methyl-1-butanol which has a sweet vinous banana flavour,
- ethyl octanoate which has a sweet apple flavour, and
- ethyl decanoate which has a caprylic fruity flavour.

Attractive flavour components are formed or are increased by 10% or more, preferably 20% or more, more preferably 30% or more, even more preferably 40% or more, and most preferably 50% or more as compared to the unprocessed pulse parts. Based on Example 7 the content of attractive flavour components in a product of the invention is min. 5% rpa, preferably at least 8% rpa, more preferably at least 10% rpa, even more preferably at least 15% rpa, and most preferably at least 20% rpa, where rpa is the relative peak area measured by headspace chromatography of the total compounds volatile at 70° C.

Protein content: The fermented protein product has a protein content of at least 25% and up to 80% by weight on dry matter basis, including 25, 30, 35, 40, 45, 50, 55, 60, 65, 70, 75, and 80%. A fraction of the protein content, about 1-35% is derived from yeasts, and about 65-99% of the protein content is derived from proteinaceous pulse parts.

A preferred protein composition is obtained using spent brewer's yeast and soya bean and/or pea and/or lupine due to the commercial and nutritional value of these raw materials.

Glyceride content: The fermented protein product has a total content of mono-, di- and triglycerides in the range of 0-30% by weight, more preferred from 0.5-23% by weight. The constituting fatty acids of the glycerides have a carbon chain length in the range of $C_8$-$C_{24}$.

The invention is illustrated in the following non-limiting Examples.

EXAMPLES

Example 1

Production and Composition of a Fermented Product Based on Defatted Soya 50.0 kg of dehulled and defatted, flash desolventised soya flakes were moistened with 10.0 kg tap water and extruded on a Werner Pfleiderer pilot extruder at 150° C. After cooling to 50° C., 60.0 kg of centrifuged, spent brewer's yeast (with approx. 10% dry matter) and 50 g of Phytase (BASF Natuphos 5000 L) were added. The resulting slurry was mixed and incubated anaerobically for 5 hours at 33° C. Next, a second incubation for 40 minutes at 85° C. was carried out in a closed system. Subsequently, the product was flash dried under such conditions that the particle temperature did not exceed 85° C. and milled in an Alpine pin mill.

The dried product had the following analysis:

| | |
|---|---|
| Crude Protein (N × 6.25) | 58.3% |
| Moisture | 5.2% |
| Crude fat | 0.9% |
| Crude fibre | 4.2% |
| Phytic acid-bound phosphorus | 0.05% |
| pH (1:10 aqueous dispersion) | 6.3 |
| Water binding | 1:4.5 |

Furthermore, anti-nutritional factors were found to be significantly reduced:

| | Raw material | Exp. product |
|---|---|---|
| Oligosaccharides | 13.5% | 0.9% |
| Trypsin Inhibitor | 62000 TIU/g | 2900 TIU/g |
| β-conglycinin | 90000 ppm | 8 ppm |
| Lectins | 200000 ppm | 1 ppm |
| Phytic acid-bound phosphorus | 0.60% | 0.05% |

The end product had a pleasant flavour and mouth feel and was easy to disperse in water. No beany taste was noted.

Example 2

Production and Composition of a Fermented Product Based on Whole Soya Beans.

10.0 kg of whole soya beans were dehulled, flaked and heated at 150° C. in a rotating drum toaster (Dantoaster). After cooling to 55° C., 6.0 kg of tap water, 3.0 kg of centrifuged, spent brewer's yeast and 10 g. of phospholipase (Lecitase from Novozymes) were admixed. The mixture was incubated anaerobically for 4 hours at 38° C. followed by 20 minutes incubation in a closed system at 92° C. After vacuum drying at 50° C. the product was finely ground on a Bühler ball mill. The ground product formed a stable suspension in water and had a pleasant flavour and mouth feel.

The dried product had the following composition:

| | |
|---|---|
| Crude protein | 42.4% |
| Crude fat | 22.4% |
| Crude fibre | 3.5% |
| Water | 4.5% |
| pH (1:10 aqueous dispersion) | 6.4 |

Example 3

Production and Composition of a Fermented Product Based on Lupine 200 g of toasted Australian lupine meal was admixed with 20 g of centrifuged brewer's yeast and 200 ml of tap water. After anaerobic incubation for 10 hours at 36° C. followed by a second incubation step in a closed system for 30 minutes at 100° C., the product was dried in a laboratory fluid bed dryer under such conditions that the particle temperature did not exceed 85° C., pin milled and analysed as shown below, in comparison with the starting material.

| | Raw material | Experimental product |
|---|---|---|
| Protein (N × 6.25) | 38.1% | 42.1% |
| Water | 9.8% | 4.7% |
| Sucrose | 4.0% | 0.0% |
| Stachyose | 6.8% | 0.8% |
| Verbascose | 1.1% | 0.2% |
| pH | 5.5 | 5.2 |
| Flavour | Beany | Acidic, pleasant |

Example 4

Production of a Fermented Protein Product by a Two-Stage Fermentation Process.

In the first batch, 1.0 kg of dehulled and defatted, flash desolventised soya flakes were mixed with 25 g live spent yeast, calculated on dry matter basis. Tap water was added to reach 60% moisture in the mixture which was placed in a closed glass jar and incubated under anaerobic conditions for 8½ hours at 45° C.

The second batch was prepared identically and run in the same way for the first 4 hours. Hereafter, atmospheric air was pumped into the fermentation jar to establish aerobic conditions during the last 4½ hours fermentation.

After the fermentations were stopped by steaming, batch samples were analysed for crude protein and carbohydrate content.

| Parameter/Method | All anaerobic | Anaerobic + Aerobic |
|---|---|---|
| Protein in dry matter, % | 58.0 | 61.5 |
| Monosaccharides, % | 5.0 | <0.5 |

It is evident from the analyses that the removal of sugars is much more efficient by a combination of anaerobic and subsequent aerobic conditions.

Example 5

Use in Animal Feed

A fermented product prepared according to Example 1 was used in piglet feed and performance compared with a control group fed with a similar feed but with soya bean meal instead of the fermented product according to this invention.

The trial was carried out with Duroc x Large White. 48 piglets were weaned at the age of 30 days, average weight 7 kg. The piglets were divided into 2 groups at random, similar body weight, genetic base, male and female. Each group was divided into 3 pens (repetitions) with 8 piglets per pen. The experiment was run for 3 weeks, during which weight gain and feed intake were recorded.

The control diet was composed of corn and normal soya bean meal. In the experimental diet, the product according to the invention replaced the normal soya bean meal. The energy level and the protein content were the same for the two diets, and the content of lysine, methionine, Ca and available phosphorus were also similar.

The diet compositions are shown in the following tables.

| Ingredient, % | Control | Experimental |
|---|---|---|
| Experimental protein product | — | 18.7 |
| Soya bean meal, 45% CP | 23.5 | — |
| Corn | 57.0 | 63.8 |
| Dried whey | 8.0 | 8.0 |
| Fish meal | 5.0 | 5.0 |
| $Ca(HPO_4)_2$ | 1.4 | 1.4 |
| $CaCO_3$ | 0.9 | 0.9 |
| 1% premix | 1.0 | 1.0 |
| Lysine HCl | 0.16 | 0.12 |
| Corn oil | 3.0 | 1.0 |

| Nutrient level | | Soybean meal | Experimental product |
|---|---|---|---|
| DE mcal/kg | | 3.34 | 3.36 |
| Crude Protein | % | 19.54 | 19.75 |
| Calcium | % | 1.02 | 0.97 |
| Available phosphorus | % | 0.49 | 0.50 |
| Lysine | % | 1.09 | 1.09 |
| Methionine | % | 0.37 | 0.37 |
| Methionine + Cysteine | % | 0.73 | 0.75 |

The trial results are shown in the table below.

| | | Control | Experiment |
|---|---|---|---|
| Start weight | kg | 7.38 ± 1.03 | 7.36 ± 1.15 |
| End weight | kg | 12.07 ± 1.44 | 12.74 ± 1.54 |
| Average daily weight gain | g | 234.10 ± 42.4 | 266.80 ± 67.5 |
| Average daily feed intake | g | 422.30 ± 48.1 | 463.10 ± 24.0 |
| Kg feed/kg gain | | 1.79 ± 0.11 | 1.67 ± 0.04 |

In conclusion, growth rate as well as feed intake and feed conversion (kg feed/kg gain) increased substantially when replacing soya bean meal with the fermented product according to the invention.

This example thus illustrates the enhanced nutritional value of the protein products according to the present invention.

The product can be used similarly as a feed product for e.g. few weeks old piglets that are being customized to eating non-dairy based feed products. These animals have a very sensitive digestive tract but upon feeding them with protein products according to the present invention, they can start earlier eating non-dairy based feed and thus gain weight at a faster rate without the risk of getting diarrhoea or other problems with the digestive system.

Example 6

Use of a Fermented Protein Product as a Functional Ingredient in Food

The functional properties of dry products produced according to the invention in food applications are demonstrated in the following example.

Thus, hamburger patties were made according to the recipes in the below table. The beef meat was ground on a 3 mm plate and mixed with salt and ⅓ of the water for ½ minute at slow speed. Next, the remaining dry ingredients were added followed by the remaining water. After another 4 minutes of mixing at slow speed patties were shaped and formed into 100 g burgers. After frying at 200° C. until a core temperature of 72° C. was reached the patties were weighed again and the frying loss calculated.

|  | Batch No. | |
| --- | --- | --- |
|  | 1 | 2 |
| Beef meat, 25% fat | 75.05% | 65.05% |
| Soya product | 0.00% | 3.00% |
| Onion flakes | 1.00% | 1.00% |
| Beef flavour | 0.20% | 0.20% |
| Salt | 1.00% | 1.00% |
| Pepper | 0.15% | 0.15% |
| Water | 22.60% | 29.60% |
|  | 100% | 100% |
| Frying loss: | 23.5% | 16.1% |

Thus, the 31.5% reduction in frying loss demonstrates the efficient water holding capacity of the experimental protein product.

Example 7

Characterisation of Flavour Profile

In order to illustrate the flavour changes obtainable by the present invention a series of products were prepared:

Based on defatted, toasted soya meal (product code A) three products according to the invention were prepared as described in Example 1 (products coded B, C and F). However, for products B and C the initial amount of yeast added to the soya meal was 3% by weight of dry matter, and for product F the initial amount of yeast added was 7% by weight of dry matter.

Likewise a product according to the invention (product code E) was prepared on the basis of full fat, toasted soya beans (product code D) as described in Example 2. However, for product E the initial amount of yeast added to the soya meal was 3% by weight of dry matter.

Product B was dried and finely ground at about 95° C., and products C, E and F were dried gently at about 85° C.

In order to characterise the flavour changes a comparative headspace gas chromatogram was made as illustrated in FIG. 1 and in the description of the drawings. Subsequently, the peak components were identified by mass spectroscopy (GC/MS-method).

1. Sampling

A 10 g sample was moisturised with water and transferred to a 100 ml gas-wash bottle. At the outlet tube a steel cylinder filled with adsorptive material i.e. Tenax, was adapted. The bottle was heated to 70° C. and the evaporated components transferred to the adsorbent material by means of a helium flow of 100 ml/min through the inlet tube for 15 minutes.

Desorption of the components for analysis was done by heating.

2. Instrumentation

Perkin Elmer ATD 400 auto sampler, HP 5890 GC with a HP 5971 MS detector.

3. GC Column 60 m CP-sil5-CB, 0.25 id. film, film thickness 1.0 μm.

4. GC Temperature Program

At 0° C. for 2 min, 10° C./min to a final temperature of 280° C., constant at 280° C. for 2 min.

5. Total Ion Current (TIC)

Scan 20-350 m/z, electron energy 70 eV.

6. Identification

The identification of the components is based on the retention time and comparison of the mass spectra with a NIST-NBS75K database.

The identification of the flavour components is listed in the following table:

| Component | Retention time in minutes |
| --- | --- |
| 1-pentanol | 18.19 |
| 1-hexanol | 20.75 |
| 1-octen-3-ol | 23.34 |
| 3-hydroxy-2-butanone | 16.74 |
| 3-methyl-1-butanol | 17.40 |
| Ethyl octanoate | 27.48 |
| Ethyl decanoate | 30.80 |

To quantify the content of the beany flavouring components (i.e. 1-pentanol, 1-hexanol and 1-octen-3-ol) and that of the favourable flavouring components (i.e. 3-hydroxy-2-butanone, 3-methyl-1-butanol, ethyl octanoate and ethyl decanoate) the relative peak area in % was recorded. The results are summarised in the following table:

| Parameter/Product | A Defatted, toasted soya meal | B Product based on A | C Product based on A | F Product based on A | D Whole, toasted soya beans | E Product based on D |
| --- | --- | --- | --- | --- | --- | --- |
| 1-pentanol | 1.1 | — | 0.3 | — | 4.2 | 1.3 |
| 1-hexanol | 18.1 | 1.0 | 1.8 | 0.1 | 23.3 | 0.7 |
| 1-octen-3-ol | 3.0 | 0.2 | 0.5 | — | 9.9 | 1.3 |
| 3-hydroxy-2-butanone | — | 4.4 | 6.4 | 0.5 | — | 3.5 |
| 3-methyl-1-butanol | 1.4 | 5.6 | 17.7 | 1.8 | 4.9 | 2.3 |
| Ethyl octanoate | — | — | 0.9 | 1.4 | — | 0.5 |

-continued

| Parameter/ Product | A Defatted, toasted soya meal | B Product based on A | C Product based on A | F Product based on A | D Whole, toasted soya beans | E Product based on D |
|---|---|---|---|---|---|---|
| Ethyl decanoate | — | 1.1 | 1.5 | 2.2 | — | 2.2 |

Note:
All figures are relative peak areas (rpa) in % of total volatile at 70° C.
Legend:
— denotes an amount below detection limit.

It is evident that the profile of volatiles of the raw materials is distinctly different from that of the resulting corresponding products according to the invention.

From the results it can be further seen that the bad smelling components are reduced by a factor of ten or more in the resulting fermented protein products. At the same time the content of the favourable flavouring components are unexpectedly significantly increased.

It is assumed that the above observation explains the markedly improved palatability of products made according to the invention, as demonstrated by the higher feed intake in Example 5.

Example 8

Use of a Fermented Protein Product in a Cosmetic Product

The fermented protein product from Example 1 was tested in a protein rich formulation intended for use in the bathtub. The composition is tabulated in the following:

| Ingredient No. | Ingredient name according to INCI | Content in % by weight |
|---|---|---|
| 1 | Sodium hexametaphosphate | 30.0 |
| 2 | Sodium sulfate | 10.5 |
| 3 | Citric acid | 0.5 |
| 4 | Coco betaine | 5.0 |
| 5 | Protein product from Example 1 | 20.0 |
| 6 | Sodium lauryl sulfate | 5.0 |
| 7 | PEG-7 glyceryl cocoate | 2.0 |
| 8 | Fragrance | 2.0 |
| 9 | Sodium chloride | 25.0 |

Procedure: Ingredients 1+2+3 are mixed and, while mixing, ingredient 4 is dosed by spraying. Under continuous mixing no. 5 is added, followed by spraying a premix of 7+8 onto the product. When the product is homogenous, the final ingredient is added, and mixing is continued until the product appears as a free flowing powder.

Example 9

Use of a Protein Product According to the Invention for the Manufacture of a Pharmaceutical Product Protein products according to the present invention are very well suited for use as a pharmaceutically acceptable ingredient in various drug formulations such as tablets and granulates. This is due to the excellent water and lipid binding properties of the product, but also due to the fact that the product is well tolerated in individuals with sensitive digestive tracts and individuals with tendencies to allergy.

The following formulation for a granulate illustrates the use of a product of the invention in a nutritional product to reduce stress induced immune suppression.

| Ingredient | Content in % by weight |
|---|---|
| Protein product from Example 1 | 40.00 |
| Corn Oil | 10.00 |
| Lecithin | 0.50 |
| Sucrose | 42.00 |
| Orange flavour | 1.50 |
| Potassium Citrate | 1.70 |
| Ascorbic Acid | 2.80 |
| Vitamin and mineral complex (B, E and Se) | 1.50 |

Before use the granulate is slurried up in water in a ratio of 1:9.

The invention claimed is:

1. A fermented protein product derived from *Saccharomyces cerevisiae* or spent brewer's yeast and one or more plant proteinaceous pulse sources prepared by a method comprising:
   (i) mixing as the sole yeast live *Saccharomyces cerevisiae* or spent brewer's yeast with one or more plant proteinaceous pulse sources in a dry matter ratio of from about 1:2 to 1:100;
   (ii) fermenting the yeast/pulse source mixture resulting from step (i) under conditions where the water content does not exceed 80%, for 1-12 hours at a temperature of about 25-60° C., under anaerobic conditions; and
   (iii) incubating the fermented mixture resulting from step (ii) for 0.5-240 minutes at a temperature of about 70-150° C. in a closed system, the incubation time being sufficient to kill all microorganisms and to inactivate remaining anti-nutritional factors, wherein a short incubation time is used at high incubation temperatures and a long incubation time is used at low incubation temperatures; wherein
   said fermented protein product has a protein content of about 25-80% by weight on a dry matter basis, wherein about 1-35% of the protein content is derived from yeast and about 65-99% of the protein content is derived from proteinaceous pulse parts,
   said fermented protein product has a glyceride content of no more than 30% by weight on a dry matter basis.

2. The fermented protein product of claim 1, wherein the method further comprises, after step (iii):
   (iv) drying the product resulting from step (iii) at a temperature not exceeding 100° C., wherein in said dried fermented protein product:
      (a) the content of one or more anti-nutritional factors selected from the group consisting of trypsin inhibitors, antigens, flatulence-producing oligosaccharides, phytic acid and lectins is reduced in amount by at least 50% compared to the unprocessed proteinaceous pulse sources;
      (b) the content of beany flavour components selected from the group consisting of 1-pentanol, 1-hexanol, and 1-octen-3-ol, and mixtures thereof is no more than 10% rpa, where rpa is the relative peak area measured by headspace chromatography of the total compounds volatile at 70° C.;
      (c) the content of flavour components selected from the group consisting of 3-hydroxy-2-butanone, 3-methyl-1-butanol, ethyl octanoate, and ethyl decanoate, is at least 5% rpa where rpa is the relative peak area measured by headspace chromatography of the total compounds volatile at 70° C.

and wherein said dried fermented protein product has a water binding capacity of at least 4 parts per part of the product by weight.

3. The fermented product according to claim 1, wherein the plant proteinaceous pulse source originates from soya, pea, lupine, a mixture of soya and pea, a mixture of soya and lupine, a mixture of pea and lupine, or a mixture of soya, pea and lupine.

4. The fermented product according to claim 1, wherein the product is dried to a water content of not more than 10% by weight and has a water binding capacity of at least 4 parts per part of the product by weight.

5. The fermented product according to claim 1, having a standard ileal digestibility measured in pigs of at least 90%.

6. The fermented product according to claim 1, which further comprises one or more edible ingredients.

7. A method of preparing a fermented protein product derived from *Saccharomyces cerevisiae* or spent brewer's yeast and one or more plant proteinaceous pulse sources, comprising:
 (i) mixing as the sole yeast live *Saccharomyces cerevisiae* or spent brewer's yeast and one or more plant proteinaceous pulse sources, in a dry matter ratio of from about 1:2 to 1:100;
 (ii) fermenting the yeast/pulse source mixture resulting from step (i) under conditions where the water content does not exceed 80%, for 1-12 hours at a temperature of about 25-60° C., under anaerobic conditions; and
 (iii) incubating the fermented mixture resulting from step (ii) for 0.5-240 minutes at a temperature of about 70-150° C. in a closed system, the incubation time being sufficient to kill all microorganisms and to inactivate remaining anti-nutritional factors, wherein a short incubation time is used at high incubation temperatures and a long incubation time is used at low incubation temperatures.

8. A method of preparing a fermented protein product derived from *Saccharomyces cerevisiae* or spent brewer's yeast and one or more plant proteinaceous pulse sources, comprising:
 (i) mixing as the sole yeast live *Saccharomyces* with plant proteinaceous pulse sources in a dry matter ratio of from about 1:2 to 1:100;
 (ii) fermenting the yeast/pulse mixture resulting from step (i) under conditions where the water content does not exceed 80%, for 1-12 hours at a temperature of about 25-60° C., under anaerobic conditions;
 (iii) fermenting the yeast/pulse mixture resulting from step (ii) under conditions where the water content does not exceed 80%, for 1-12 hours at a temperature of about 25-60° C., under aerobic conditions; and
 (iv) incubating the fermented mixture resulting from step (iii) for 0.5-240 minutes at a temperature of about 70-150° C. in a closed system, the incubation time being sufficient to kill all microorganisms and to inactivate remaining anti-nutritional factors, wherein a short incubation time is used at high incubation temperatures and a long incubation time is used at low incubation temperatures.

9. The method according to claim 7, wherein one or more enzymes selected from the group consisting of proteases, peptidases, galactosidases, amylases, pectinases, hemicellulases, phytases, lipases, and phospholipases are added in any of steps (i) to (iii).

10. The method according to claim 7, wherein the plant proteinaceous pulse sources originate from soya, pea, lupine, a mixture of soya and pea, a mixture of soya and lupine, a mixture of pea and lupine, or a mixture of soya, pea and lupine.

11. The method according to claim 7, further comprising a step where the mixture obtained in step (iii) is subjected to drying and milling under such conditions that particles in the mixture do not exceed a temperature of 100° C.

12. The method according to claim 7, further comprising drying the mixture from step (iii) to obtain a product having a water content of not more than 10% by weight, wherein the product has a water binding capacity of at least 4 parts per part of the product by weight.

13. The method according to claim 7, wherein the protein content of the product obtained from step (iii) is 25-80% by weight on a dry matter basis, and wherein the glyceride content is no more than 30% by weight on a dry matter basis.

14. The method according to claim 7, wherein about 1-35% of the protein content of the product obtained from step (iii) is derived from yeast protein and about 65-99% of the protein content is derived from plant proteinaceous pulse sources.

15. The method according to claim 7, wherein the product obtained from step (iii) contains an anti-nutritional factor selected from the group consisting of trypsin inhibitors, antigens, flatulence-producing oligosaccharides, phytic acid, and lectins, the anti-nutritional factor being reduced in amount by at least 50% as compared to unprocessed plant proteinaceous pulse sources.

16. The method according to claim 7, wherein the product obtained from step (iii) contains a beany flavour component selected from the group consisting of 1-pentanol, 1-hexanol, and 1-octen-3-ol, the beany flavour component being reduced by at least 50% as compared to unprocessed plant proteinaceous pulse sources.

17. The method according to claim 7, wherein the product obtained from step (iii) comprises at least one flavor component selected from the group consisting of 3-hydroxy-2-butanone, 3-methyl-1-butanol, ethyl octanoate, and ethyl decanoate, the flavor component being formed or increased in amount by 10% or more, as compared to unprocessed plant proteinaceous pulse sources.

18. The method according to claim 7, wherein the product obtained from step (iii) contains beany flavour components selected from the group consisting of 1-pentanol, 1-hexanol, and 1-octen-3-ol, the beany flavour components being no more than 10% rpa, where rpa is the relative peak area measured by headspace chromatography of the total compounds volatile at 70° C.

19. The method according to claim 7, wherein the product obtained in step (iii) includes flavour components selected from the group consisting of 3-hydroxy-2-butanone, 3-methyl-1-butanol, ethyl octanoate, and ethyl decanoate which are newly formed or increased to a content of min. 5% rpa, where rpa is the relative peak area measured by headspace chromatography of the total compounds volatile at 70° C.

20. The method according to claim 7, further comprising adding one or more edible ingredients to the product.

21. A processed food product for human or animal consumption, comprising a fermented protein product according to claim 1.

22. The processed food product according to claim 21, wherein the processed food product is a milk replacer.

23. A processed food or feed product with improved functional properties comprising a fermented protein product according to claim 1.

24. A food or feed product for individuals with a sensitive digestive tract and/or individuals having or being at risk of developing allergies, comprising a fermented protein product according to claim 1.

25. A cosmetic product comprising the fermented protein product according to claim 1.

26. A pharmaceutical product, comprising the fermented protein product according to claim 1.

27. A processed food product for human or animal consumption containing from 1 to 99% by weight of a fermented protein product according to claim 1.

28. A cosmetic or pharmaceutical product containing from 1 to 99% by weight of a fermented protein product according to claim 1.

29. The fermented protein product according to claim 1, wherein the glyceride content is 0.5-23% by weight on dry matter basis.

30. The fermented protein product according to claim 1, wherein the fermented protein product includes an anti-nutritional factor selected from the group consisting of trypsin inhibitors, antigens, flatulence-producing oligosaccharides, phytic acid and lectins, the anti-nutritional factor being reduced in amount by at least 90% as compared to unprocessed plant proteinaceous pulse sources.

31. The fermented protein product according to claim 1, wherein the fermented protein product includes a beany flavour component selected from the group consisting of 1-pentanol, 1-hexanol, and 1-octen-3-ol, the beany flavour component being reduced in amount by at least 75% as compared to unprocessed plant proteinaceous pulse sources.

32. The fermented protein product according to claim 1, wherein attractive flavour component selected from the group consisting of 3-hydroxy-2-butanone, 3-methyl-1-butanol, ethyl octanoate, and ethyl decanoate, the attractive flavour component being formed is increased by at least 50% as compared to unprocessed plant proteinaceous pulse sources.

33. The fermented protein product according to claim 2, wherein the glyceride content is 0.5-23% by weight on dry matter basis.

34. The fermented protein product according to claim 2, wherein the anti-nutritional factor is reduced in amount by at least 90% as compared to unprocessed plant proteinaceous pulse sources.

35. The fermented protein product according to claim 2, wherein the beany flavour component selected from the group consisting of 1-pentanol, 1-hexanol, and 1-octen-3-ol is reduced in amount by at least 75% as compared to unprocessed plant proteinaceous pulse sources.

36. The fermented protein product according to claim 2, wherein the attractive flavour component selected from the group consisting of 3-hydroxy-2-butanone, 3-methyl-1-butanol, ethyl octanoate, and ethyl decanoate is formed or is increased in amount by at least 50% as compared to unprocessed plant proteinaceous pulse sources.

37. The fermented protein product according to claim 2, the beany flavour components being no more than 5% rpa, where rpa is the relative peak area measured by headspace chromatography of the total compounds volatile at 70° C.

38. The fermented protein product according to claim 2, the attractive flavour components being at least 8% rpa, where rpa is the relative peak area measured by headspace chromatography of the total compounds volatile at 70° C.

39. The fermented product according to claim 2, wherein the plant proteinaceous pulse sources portion originates from soya, pea, lupine, a mixture of soya and pea, a mixture of soya and lupine, a mixture of pea and lupine, or a mixture of soya, pea and lupine.

40. The fermented product according to claim 2, wherein the product is dried to a water content of not more than 10% by weight.

41. The fermented product according to claim 2, having a standard ileal digestibility measured in pigs of at least 90%.

42. The fermented product according to claim 2, which further comprises one or more edible ingredients.

43. The method according to claim 7, wherein the temperature in step (ii) is about 25-45° C.

44. The method according to claim 8, wherein the temperature in step (ii) is about 25-45° C.

45. The method according to claim 8, wherein the temperature in step (iii) is about 30-60° C.

46. The method according to claim 8, wherein one or more enzymes selected from the group consisting of proteases, peptidases, galactosidases, amylases, pectinases, hemicellulases, phytases, lipases, and phospholipases are added in any of steps (i) to (iv).

47. The method according to claim 8, wherein the plant proteinaceous pulse sources originate from soya, pea, lupine, a mixture of soya and pea, a mixture of soya and lupine, a mixture of pea and lupine, or a mixture of soya, pea and lupine.

48. The method according to claim 7, wherein the product obtained in step (iii) is subjected to drying and milling under such conditions that particles in the mixture do not exceed a temperature of 70° C.

49. The method according to claim 8, wherein the product obtained in step (iv) is subjected to drying and milling under such conditions that particles in the mixture do not exceed a temperature of 100° C.

50. The method according to claim 8, wherein the product obtained in step (iv) is subjected to drying and milling under such conditions that particles in the mixture do not exceed a temperature of 70° C.

51. The method according to claim 8, wherein the product obtained from step (iv) has a water content of not more than 10% by weight, and a water binding capacity of at least 4 parts per part of the product by weight.

52. The method according to claim 2, wherein the protein content of the product obtained from step (iv) is 25-80% by weight on dry matter basis, and wherein the glyceride content of the product is no more than 30% by weight on dry matter basis.

53. The method according to claim 8, wherein about 1-35% of the protein content of the product obtained from step (iv) is derived from yeast protein and about 65-99% of the protein content is derived from plant proteinaceous pulse sources.

54. The method according to claim 15, wherein the anti-nutritional factor is reduced by an amount of at least 90% compared to unprocessed plant proteinaceous pulse sources.

55. The method according to claim 16, wherein a beany flavor component selected from the group consisting of 1-pentanol, 1-hexanol, and 1-octen-3-ol is reduced in amount by at least 90% as compared to unprocessed pulse parts.

56. The method according to claim 8, wherein the product obtained from step (iv) contains a beany flavour component selected from the group consisting of 1-pentanol, 1-hexanol, and 1-octen-3-ol, wherein the beany flavour component is reduced in amount by at least 50% as compared to unprocessed plant proteinaceous pulse sources.

57. The method according to claim 56, wherein the beany flavour component selected from the group consisting of 1-pentanol, 1-hexanol, and 1-octen-3-ol is reduced in amount by at least 90% as compared to unprocessed plant proteinaceous pulse sources.

58. The method according to claim 17, wherein the attractive flavor component selected from the group consisting of 3-hydroxy-2-butanone, 3-methyl-1-butanol, ethyl octanoate, and ethyl decanoate is formed or increased in amount by at least 50% as compared to unprocessed plant proteinaceous pulse sources.

59. The method according to claim 8, wherein the product obtained from step (iv) contains an attractive flavour component selected from the group consisting of 3-hydroxy-2-butanone, 3-methyl-1-butanol, ethyl octanoate, and ethyl decanoate, wherein the attractive flavor component is formed or increased in amount by at least 10%, as compared to unprocessed plant proteinaceous pulse sources.

60. The method according to claim 59, wherein the attractive flavour component selected from the group consisting of 3-hydroxy-2-butanone, 3-methyl-1-butanol, ethyl octanoate, and ethyl decanoate is formed or is increased in amount by at least 50% as compared to unprocessed plant proteinaceous pulse sources.

61. The method according to claim 18, wherein the beany flavour components are reduced to no more than 5% rpa, where rpa is the relative peak area measured by headspace chromatography of the total compounds volatile at 70° C.

62. The method according to claim 8, wherein the product obtained from step (iv) contains one or more beany flavour components selected from the group consisting of 1-pentanol, 1-hexanol, and 1-octen-3-ol, wherein the beany flavour components are reduced to no more than 10% rpa, where rpa is the relative peak area measured by headspace chromatography of the total compounds volatile at 70° C.

63. The method according to claim 62, wherein the beany flavour components are reduced to no more than 5% rpa, where rpa is the relative peak area measured by headspace chromatography of the total compounds volatile at 70° C.

64. The method according to claim 19, wherein the attractive flavour components are newly formed or increased to a content of 8% rpa, where rpa is the relative peak area measured by headspace chromatography of the total compounds volatile at 70° C.

65. The method according to claim 8, wherein the product obtained from step (iv) contains one or more attractive flavour components selected from the group consisting of 3-hydroxy-2-butanone, 3-methyl-1-butanol, ethyl octanoate, and ethyl decanoate, wherein the attractive flavour components are newly formed or increased in amount to at least 5% rpa, where rpa is the relative peak area measured by headspace chromatography of the total compounds volatile at 70° C.

66. The method according to claim 65, the attractive flavour components being newly formed or being increased in amount to at least 8% rpa, where rpa is the relative peak area measured by headspace chromatography of the total compounds volatile at 70° C.

67. The method according to claim 8, further comprising adding one or more edible ingredients to the product obtained in step (iv).

68. A processed food product for human or animal consumption containing from 1 to 99% by weight of a fermented protein product according to claim 2.

69. A processed food product for human or animal consumption containing from 1 to 99% by weight of a fermented protein prepared by the method according to claim 7.

70. A processed food product for human or animal consumption containing from 1 to 99% by weight of a fermented protein prepared by the method according to claim 8.

71. A cosmetic or pharmaceutical product containing from 1 to 99% by weight of the fermented protein product according to claim 2.

72. A cosmetic or pharmaceutical product containing from 1 to 99% by weight of the fermented protein product prepared by the method according to claim 7.

73. A cosmetic or pharmaceutical product containing from 1 to 99% by weight of the fermented protein product prepared by the method according to claim 8.

74. The fermented protein product of claim 1, wherein:
(a) the content of at least on anti-nutritional factor selected from the group consisting of trypsin inhibitors, antigens, flatulence-producing oligosaccharides, phytic acid and lectins is reduced by at least 50% compared to the unprocessed proteinaceous pulse sources;
(b) the content of at least one beany flavor compound selected from the group consisting of 1-pentanol, 1-hexanol, and 1-octen-3-ol is reduced by at least 50% as compared to the unprocessed proteinaceous pulse sources; and
(c) the content of at least one flavor compound selected from the group consisting of 3-hydroxy-2-butanone, 3-methyl-1-butanol, ethyl octanoate, and ethyl decanoate is increased by at least 10% as compared to the unprocessed proteinaceous pulse sources.

* * * * *